(12) United States Patent
Gomi et al.

(10) Patent No.: US 9,238,373 B2
(45) Date of Patent: Jan. 19, 2016

(54) FLUID EJECTION DEVICE

(71) Applicant: SEIKO EPSON CORPORATION, Tokyo (JP)

(72) Inventors: Masaki Gomi, Hino (JP); Kazuaki Uchida, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/682,928

(22) Filed: Apr. 9, 2015

(65) Prior Publication Data
US 2015/0290949 A1 Oct. 15, 2015

(30) Foreign Application Priority Data
Apr. 10, 2014 (JP) ................................ 2014-080821

(51) Int. Cl.
- B41J 2/175 (2006.01)
- B41J 2/195 (2006.01)
- B41J 29/393 (2006.01)
- B29C 45/20 (2006.01)

(52) U.S. Cl.
CPC .................................. B41J 2/17596 (2013.01)

(58) Field of Classification Search
CPC .... B41J 2/175; B41J 2/14274; B41J 2/17546; B41J 2/17596; B41J 2/355; A61B 2017/00154; A61B 2017/113; F04B 43/06; F04B 43/046; F04B 43/073; F04B 3/10; F04B 43/107; F04B 43/113
USPC ........ 347/7, 10, 11, 19, 84, 85; 239/1, 87, 88, 239/91, 92, 118, 337; 222/1, 258, 282
See application file for complete search history.

(56) References Cited

U.S. PATENT DOCUMENTS

| | | | | |
|---|---|---|---|---|
| 6,435,638 | B1 * | 8/2002 | Wilson | B41J 2/17513 347/7 |
| 7,044,579 | B2 * | 5/2006 | Katsuumi | B41J 2/16532 347/29 |
| 7,794,032 | B2 * | 9/2010 | Kimura | B41J 2/175 347/7 |
| 7,950,785 | B2 * | 5/2011 | Usuda | B41J 2/17556 347/7 |
| 9,005,227 | B2 * | 4/2015 | Kojima | A61B 17/3203 606/167 |
| 2011/0006127 | A1 | 1/2011 | Ono et al. | |

FOREIGN PATENT DOCUMENTS

| | | |
|---|---|---|
| EP | 2 158 930 A1 | 3/2010 |
| EP | 2 476 383 A2 | 7/2012 |
| JP | 2010-059939 A | 3/2010 |

OTHER PUBLICATIONS

European Search Report for European Application No. EP 15 16 6752, mailed Jun. 5, 2015.

* cited by examiner

Primary Examiner — Anh T.N. Vo
(74) Attorney, Agent, or Firm — Maschoff Brennan

(57) ABSTRACT

A fluid ejection device includes a fluid storing unit and a fluid outlet. A fluid pressing unit presses the fluid storing unit and causes fluid to flow from the fluid outlet. A connection pipe has an end that is connected to the fluid outlet. A fluid ejection unit ejects the fluid, which is received from a fluid intake port to which the other end of the connection pipe is connected, in a pulse-like manner according to a drive signal generated by a fluid-ejecting control unit. An ejecting-instruction input unit receives a fluid ejecting instruction. If the pressure in the fluid storing unit is equal to or higher than an upper limit value in a range determined with reference to a target pressure value, the drive signal is not generated. When the pressure in the fluid storing unit is lower than the upper limit value, the drive signal is generated.

5 Claims, 7 Drawing Sheets

FLUID EJECTION DEVICE

This application claims the benefit of Japanese Patent Application No. 2014-080821, filed on Apr. 10, 2014. The content of the aforementioned application is incorporated herein by reference in its entirety.

BACKGROUND

1. Technical Field

The present invention relates to a fluid ejection device.

2. Related Art

There is known a technique for ejecting fluid in a pulse-like manner to perform incision, excision, or the like of a target object. For example, in the medical field, as a surgical instrument for incising or excising a biological tissue, there is proposed a fluid ejection device including a pulsed flow generating unit that ejects fluid in a pulse-like manner, a fluid supplying unit that supplies the fluid to the pulsed flow generating unit, a fluid supply path that connects the fluid supplying unit and the pulsed flow generating unit, and an operation switch that switches ON and OFF of the ejecting (see, for example, JP-A-2010-059939 (Patent Literature 1)).

The fluid ejection device increases a driving voltage for a piezoelectric element in the pulsating-current generating unit stepwise to increase ejecting strength of the fluid stepwise and prevents a target region from being cut too deeply.

However, the ejecting strength of the fluid is also affected by the pressure of the fluid in the fluid supplying unit. When the operation switch is operated, the pressure in the fluid supplying unit is not always appropriate.

For example, when the operation switch is operated in a state in which the pressure of the fluid in the fluid supplying unit is too high, it is likely that strong ejecting not intended by a surgeon is performed.

Therefore, there is a demand for a technique for not performing the ejecting of the fluid when the pressure in the fluid supplying unit is equal to or higher than a predetermined upper limit value determined according to ejecting strength and capable of improving the safety of the fluid ejection device.

SUMMARY

A fluid ejection device according to an aspect of the invention includes: a fluid container including a fluid storing unit that stores fluid and a fluid outlet formed in the fluid storing unit; a fluid pressing unit configured to press the fluid storing unit and cause the fluid to flow out from the fluid outlet; a connection pipe, one end of which is connected to the fluid outlet; a fluid ejection unit including a fluid intake port, to which the other end of the connection pipe is connected, and configured to eject the fluid, which is taken in from the fluid intake port, in a pulse-like manner according to a drive signal; a pressure detecting unit configured to detect pressure in the fluid storing unit; an ejecting-strength input unit configured to receive an input for setting ejecting strength of the ejecting of the fluid by the fluid ejection unit; a pressing control unit configured to control the fluid pressing unit to bring the pressure in the fluid storing unit close to a target pressure value determined according to the ejecting strength; an ejecting-instruction input unit configured to receive an instruction input for ejecting the fluid from the fluid ejection unit; and a fluid-ejecting control unit configured to output the drive signal to the fluid ejection unit. When the ejecting-instruction input unit receives the instruction input, if the pressure in the fluid storing unit is equal to or higher than an upper limit value in a first predetermined range determined with reference to the target pressure value, the fluid-ejecting control unit does not output the drive signal. When the pressure in the fluid storing unit is lower than the upper limit value, the fluid-ejecting control unit outputs the drive signal.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Overview

Figure 1:
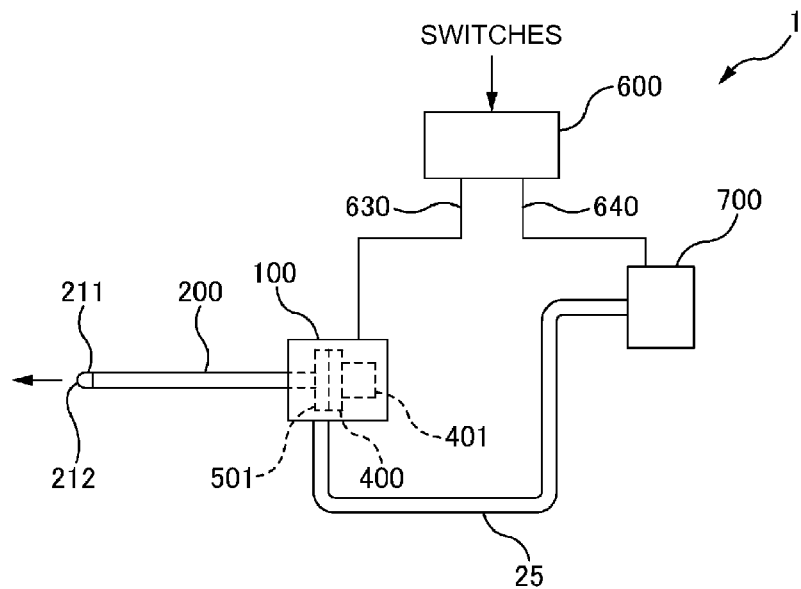
FIG. 1 is a block diagram showing an example of the overall configuration of a fluid ejection device according to an embodiment of the invention.

At least matters described below are made apparent by the description of this specification and the drawings.

A fluid ejection device includes: a fluid container including a fluid storing unit that stores fluid and a fluid outlet formed in the fluid storing unit; a fluid pressing unit configured to press the fluid storing unit and cause the fluid to flow out from the fluid outlet; a connection pipe, one end of which is connected to the fluid outlet; a fluid ejection unit including a fluid intake port, to which the other end of the connection pipe is connected, and configured to eject the fluid, which is taken in from the fluid intake port, in a pulse-like manner according to a drive signal; a pressure detecting unit configured to detect pressure in the fluid storing unit; an ejecting-strength input unit configured to receive an input for setting ejecting strength of the ejecting of the fluid by the fluid ejection unit; a pressing control unit configured to control the fluid pressing unit to bring the pressure in the fluid storing unit close to a target pressure value determined according to the ejecting strength; an ejecting-instruction input unit configured to receive an instruction input for ejecting the fluid from the fluid ejection unit; and a fluid-ejecting control unit configured to output the drive signal to the fluid ejection unit. When the ejecting-instruction input unit receives the instruction input, if the pressure in the fluid storing unit is equal to or higher than an upper limit value in a first predetermined range determined with reference to the target pressure value, the fluid-ejecting control unit does not output the drive signal. When the pressure in the fluid storing unit is lower than the upper limit value, the fluid-ejecting control unit outputs the drive signal.

With such a fluid ejection device, it is possible not to perform the ejecting of the fluid when the pressure in the fluid storing unit is equal to or higher than the predetermined upper limit value determined according to the ejecting strength. It is possible to improve the safety of the fluid ejection device.

It is preferable that, after the pressure in the fluid storing unit reaches the target pressure value, if the pressure is within a second predetermined range narrower than the first predetermined range determined with reference to the target pressure value, even if the pressure is different from the target pressure value, the pressing control unit does not perform the control for bringing the pressure close to the target pressure value.

With such a fluid ejection device, it is possible to prevent the control from being continued indefinitely, for example, irrespective of the fact that a difference between the pressure in the fluid storing unit and the target pressure value is, for example, a very small difference not affecting the ejecting strength.

It is preferable that, after the pressure in the fluid storing unit reaches the target pressure value, if the pressure is within the first predetermined range but is outside the second predetermined range, the pressing control unit controls the fluid pressing unit such that the pressure falls within the second predetermined range.

With such a fluid ejection device, it is possible to stop the control of the pressure at a point in time when the pressure falls within the second predetermined range. Therefore, it is possible to keep the pressure within the second predetermined range even if, for example, overshoot of the pressure occurs. It is possible to improve the accuracy of the pressure control.

It is preferable that, while the fluid-ejecting control unit is outputting the drive signal, the pressing control unit controls the fluid pressing unit such that a predetermined amount of the fluid flows out per unit time from the fluid container.

With such a fluid ejection device, when the fluid ejection unit ejects the fluid, it is possible to eliminate pressure fluctuation in the fluid storing unit involved in feedback control and supply a stable amount of the fluid to the fluid ejection unit. Therefore, it is possible to eject the fluid from the fluid ejection unit at stable strength.

It is preferable that the fluid ejection device further includes a channel opening and closing unit configured to open and close a channel of the fluid in the connection pipe, and the pressing control unit performs, by causing, in a state in which the channel is closed by the fluid opening and closing unit, the fluid pressing unit to press the fluid storing unit, the control for bringing the pressure in the fluid storing unit close to the target pressure value.

With such a fluid ejection device, it is possible to accurately bring the pressure in the fluid storing unit close to the target pressure value.

Overall Configuration

An embodiment of the invention is explained below with reference to the drawings. A fluid ejection device according to this embodiment is adoptable for cleaning, cutting, and the like of fine objects, structures, biological tissues, and the like. In the embodiment explained below, a fluid ejection device suitable for a surgical knife for incising or excising a biological tissue is illustrated. Therefore, fluid used in the fluid ejection device according to this embodiment is water, saline, predetermined chemical, or the like. Note that, drawings referred to in the following explanation are schematic diagrams in which, for convenience of illustration, longitudinal and lateral scales of members and portions are different from actual scales.

FIG. 1 is a schematic explanatory diagram showing a fluid ejection device 1 functioning as a surgical knife according to this embodiment. The fluid ejection device 1 according to this embodiment includes a pump 700 that supplies fluid, a pulsation generator (a fluid ejection unit) 100 that converts the fluid supplied from the pump 700 into a pulsed flow and ejects the fluid in a pulse-like manner, a driving control unit (a fluid-ejecting control unit) 600 that performs control of the fluid ejection device 1 in cooperation with the pump 700, and a connection tube 25 functioning as a connection route (a connection pipe) that connects the pump 700 and the pulsation generator 100 to form a channel through which the fluid flows.

As explained in detail below, the pulsation generator 100 includes a fluid chamber 501 in which the fluid supplied from the pump 700 is stored, a diaphragm 400 that changes the volume of the fluid chamber 501, and a piezoelectric element 401 that vibrates the diaphragm 400.

The pulsation generator 100 includes a thin pipe-like fluid ejecting pipe 200 functioning as a channel of the fluid ejected from the fluid chamber 501 and a nozzle 211 with a reduced channel diameter attached to the distal end portion of the fluid ejecting pipe 200.

The pulsation generator 100 drives the piezoelectric element 401 with a drive signal output from the driving control unit 600, changes the volume of the fluid chamber 501 to apply pressure to the fluid in a pulse-like manner and convert the fluid into a pulsed flow, and ejects the fluid in a pulse-like manner at high speed through the fluid ejecting pipe 200 and the nozzle 211.

The driving control unit 600 and the pulse generating unit 100 are connected by a control cable 630. A driving single for driving the piezoelectric element 401 output from the driving control unit 600 is transmitted to the pulsation generator 100 via the control cable 630.

The driving control unit 600 and the pump 700 are connected by a communication cable 640. The driving control unit 600 and the pump 700 exchange various commands and data each other according to a predetermined communication protocol such as a CAN (Controller Area Network).

The driving control unit 600 receives inputs of signals from various switches operated by a surgeon or the like who performs a surgical operation using the pulsation generators 100. The driving control unit 600 controls the pump 700 and the pulsation generator 100 via the control cables 630 and the communication cable 640.

As the switches connected to the driving control unit 600, there are, for example, a pulsation-generating-unit start switch (an ejecting-instruction input unit) 625, an ejecting-strength changeover switch (an ejecting-strength input unit) 627, and a flushing switch 628 (not shown in the figure).

The pulsation-generating-unit start switch 625 is a switch for switching presence or absence of ejecting of the fluid from the pulsation generator 100. When the pulsation-generating-unit start switch 625 is operated by the surgeon who performs a surgical operation using the pulsation generators 100, the driving control unit 600 executes control for ejecting the fluid or stopping the ejecting of the fluid from the pulsation generator 100 in cooperation with the pump 700. The pulsation-generating-unit start switch 625 can take a form of a footswitch operated by the foot of the surgeon or can take a form of being disposed integrally with the pulsation generator 100, which is gripped by the surgeon, and operated by the hand and the fingers of the surgeon.

The ejecting-strength changeover switch 627 is a switch for setting ejecting strength of the fluid ejected from the pulsation generator 100. When the ejecting-strength-changeover switch 627 is operated, the driving control unit 600 applies control for increasing or reducing the ejecting strength of the fluid to the pulsation generator 100 and the pump 700.

For example, when causing the pulsation generator 100 to eject the fluid, the driving control unit 600 outputs, to the pulsation generator 100, a drive signal of a voltage corresponding to the ejecting strength set by the ejecting-strength changeover switch 627. For example, the driving control unit 600 increases a driving voltage when the ejecting strength is increased and reduces a driving voltage when the ejecting strength is reduced.

When supplying the fluid to the pulsation generator 100, the pump 700 controls the pressure of the fluid in the pump 700 to be pressure corresponding to the ejecting strength set by the ejecting-strength changeover switch 627. For example, the pump 700 increases the pressure of the fluid when the ejecting strength is increased and reduces the pressure of the fluid when the ejecting strength is reduced.

The flushing switch 628 is explained below.

In this embodiment, the pulsed flow means flowing of the fluid that flows in a fixed direction and involves cyclic or irregular fluctuation of a flow rate or flow velocity of the fluid. The pulsed flow also includes an intermittent flow that repeats flowing and stop of the fluid. However, since the flow rate or the flow velocity of the fluid only has to cyclically or irregularly fluctuates, the pulsed flow does not always need to be the intermittent flow.

Similarly, ejecting the fluid in a pulse-like manner means ejecting of the fluid, the flow rate or the flow velocity of which cyclically or irregularly fluctuates. Examples of the pulse-like ejecting include intermittent ejecting that repeats ejecting and non-ejecting of the fluid. However, since the flow rate or the flow velocity of the ejected fluid only has to cyclically or irregularly fluctuates, the ejecting of the fluid does not always need to be intermittent ejecting.

When the pulsation generator 100 stops the driving, that is, when the pulsation generator 100 does not change the volume of the fluid chamber 501, the fluid supplied from the pump 700 functioning as a fluid supplying unit at predetermined pressure continuously flows out from the nozzle 211 through the fluid chamber 501.

Note that the fluid ejection device 1 according to this embodiment may include a plurality of pumps 700. For example, a configuration in which the fluid ejection device 1 includes two pumps 700 is illustrated in FIG. 2.

Figure 2:
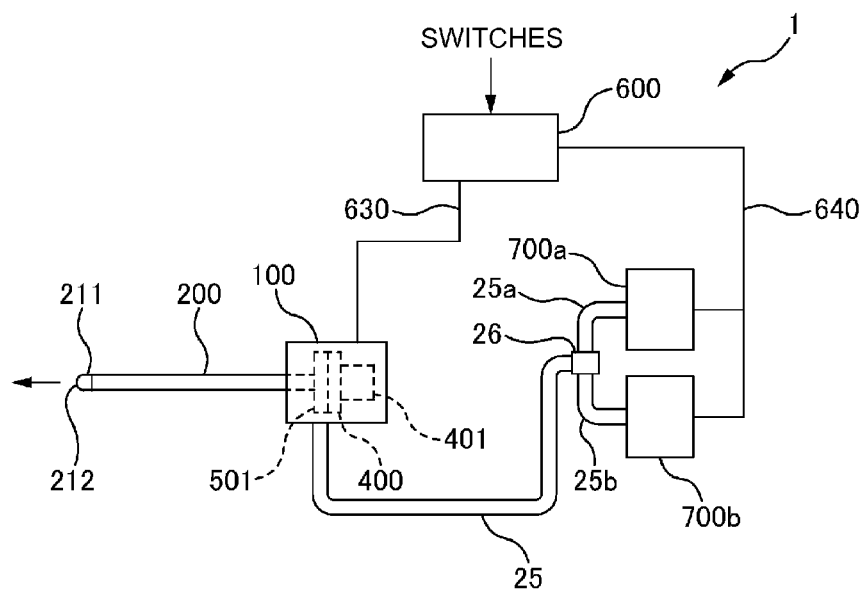
FIG. 2 is a block diagram showing another example of the overall configuration of the fluid ejection device according to the embodiment of the invention.

In this case, as shown in FIG. 2, the fluid ejecting device 1 includes a first pump 700a and a second pump 700b. A connection route (a connection pipe) that connects the pulsation generator 100, the first pump 700a, and the second pump 700b to form a channel through which the fluid flows is configured by a first connection tube 25a, a second connection tube 25b, a connection tube 25, and a three-way stopcock 26.

A valve configured to be capable of switching whether the first connection tube 25a and the connection tube 25 are caused to communicate with each other or the second connection tube 25b and the connection tube 25 are caused to communicate with each other is used as the three-way stopcock 26. Any one of the first pump 700a and the second pump 700b is selectively used.

With such a configuration, for example, when the first pump 700a is selectively used, if the supply of the fluid from the first pump 700a cannot be performed because of some reason such as a failure, the three-way stopcock 26 is switched to cause the second connection tube 25b and the connection tube 25 to communicate with each other and then the supply of the fluid from the second pump 700b is started. Consequently, it is possible to continuously use the fluid ejection device 1. It is possible to minimize the influence of the inability of the supply of the fluid from the first pump 700.

Note that, in the following explanation, even if the fluid ejection device 1 includes the plurality of pumps 700, when it is unnecessary to distinguish and explain the pumps 700, the pumps 700 are collectively referred to as pump 700.

On the other hand, when it is necessary to distinguish and explain the respective plurality of pumps 700, the pumps 700 are distinguished and shown like the first pump 700a, the second pump 700b, and the like. Suffixes such as "a" and "b" are added to reference numeral 700 of the pumps 700. In this case, the suffix "a" is added to reference numerals of components in the first pump 700a and the suffix "b" is added to reference numerals of components of the second pump 700b.

Pump

An overview of the configuration and the operation of the pump 700 according to this embodiment is explained with reference to FIG. 3.

The pump 700 according to this embodiment includes a pump control unit (a pressing control unit) 710, a slider 720, a motor 730, a linear guide 740, and a pinch valve (a channel opening and closing unit) 750. The pump 700 includes a fluid-container attaching unit 770 for detachably attaching a fluid container 760 that stores the fluid. The fluid-container attaching unit 770 is formed to hold the fluid container 760 in a specified position when the fluid container 760 is attached.

As explained in detail below, signals from a slider release switch 780, a slider set switch 781, a fluid-feed ready switch 782, a priming switch 783, and a pinch valve switch 785 are connected to the pump control unit 710 (not shown in the figure).

In this embodiment, as an example, the fluid container 760 is configured as an injection cylinder including a syringe 761 and a plunger 762.

In the fluid container 760, an opening section 764 (fluid outlet) having a projected cylindrical shape is formed at the distal end portion of the syringe 761. When the fluid container 760 is attached to the fluid-container attaching unit 770, an end portion of the connection tube 25 is fit in the opening section 764 to form a channel of the fluid from the inside of the syringe 761 to the connection tube 25.

The pinch valve 750 is a valve that is provided on a route of the connection tube 25 and opens and closes a channel of the fluid between the fluid container 760 and the pulsation generator 100.

Opening and closing of the pinch valve 750 is performed by the control unit 710. When the pump control unit 710 opens the pinch valve 750, the fluid container 760 and the pulsation generator 100 communicate with each other through the channel. When the pump control unit 710 closes the pinch valve 750, the channel between the fluid container 760 and the pulsation generator 100 is blocked.

After the fluid container 760 is attached to the fluid-container attaching unit 770, when the plunger 762 of the fluid container 760 is moved in a direction for pushing the plunger 762 into the syringe 761 (hereinafter also referred to as push-in direction) in a state in which the pinch valve 750 is opened, the volume of a space (hereinafter also referred to as fluid storing unit 765) surrounded by an end face of a gasket 763, which is made of resin such as rubber having elasticity, attached to the distal end on the push-in direction side of the plunger 762 and the inner wall of the syringe 761 decreases. The fluid filled in the fluid storing unit 765 is ejected from the opening section 764 at the distal end portion of the syringe 761. The fluid ejected from the opening section 764 is filled in the connection tube 25 and supplied to the pulsation generator 100.

On the other hand, after the fluid container 760 is attached to the fluid-container attaching unit 770, when the plunger 762 of the fluid container 760 is moved in the push-in direction in a state in which the pinch valve 750 is closed, the volume of the fluid storing unit 765 surrounded by the gasket 763 attached to the distal end of the plunger 762 and the inner wall of the syringe 761 decreases. The pressure of the fluid filled in the fluid storing unit 765 can be increased.

The movement of the plunger 762 is performed by the pump control unit 710 moving the slider 720 along a direction in which the plunger 762 slides when the fluid container 760 is attached to the fluid-container attaching unit 770 (the push-in direction and the opposite direction of the push-in direction).

Specifically, the slider 720 is attached to the linear guide 740 to engage a pedestal section 721 of the slider 720 to a rail (not shown in the figure) linearly formed in the linear guide 740 along the sliding direction of the plunger 762. The linear guide 740 moves the pedestal section 721 of the slider 720 along the rail using power transmitted from the motor 730 driven by the pump control unit 710, whereby the slider 720 moves in the sliding direction of the plunger 762.

Figure 3:
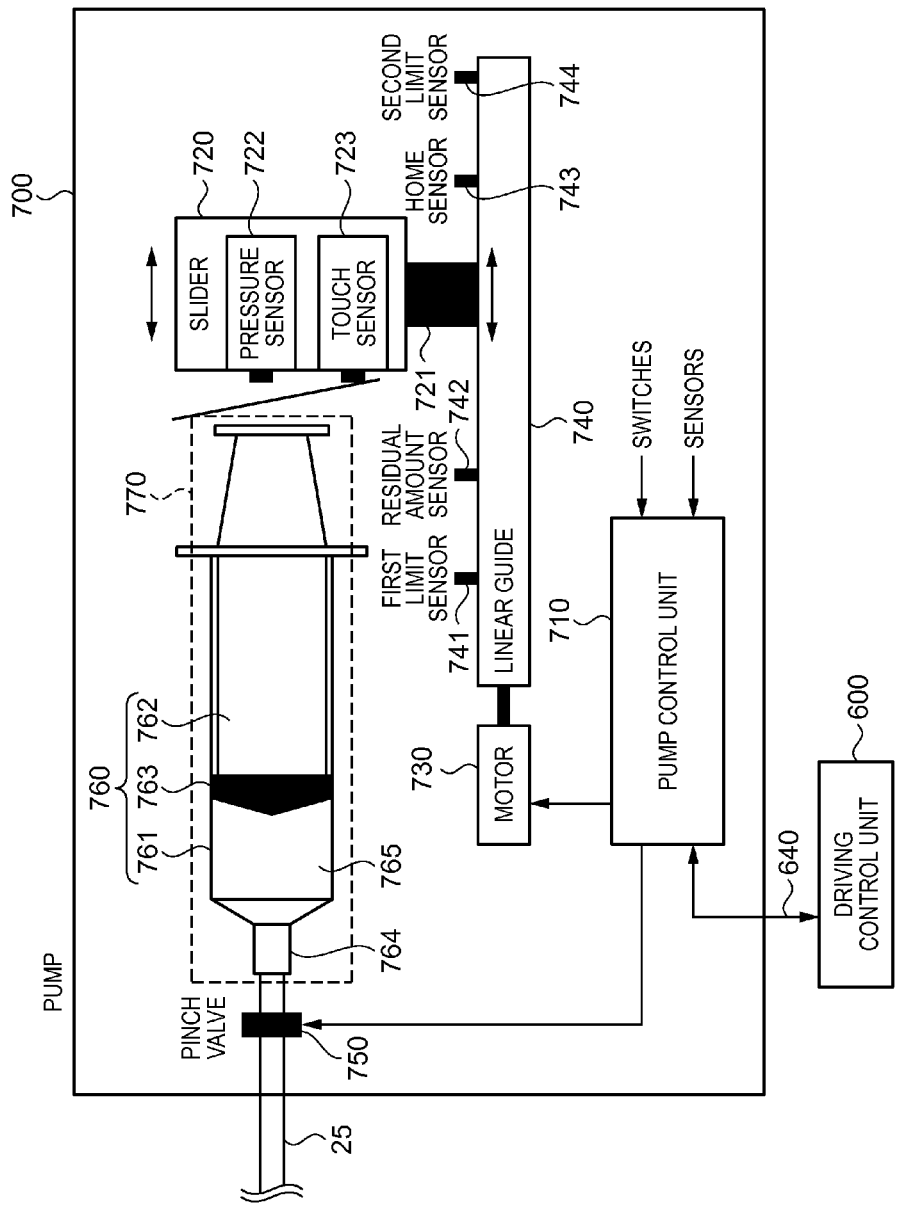
FIG. 3 is a block diagram showing the configuration of a pump according to the embodiment of the invention.

As shown in FIG. 3, a first limit sensor 741, a residual amount sensor 742, a home sensor 743, and a second limit sensor 744 are provided along the rail of the linear guide 740.

All of the first limit sensor 741, the residual amount sensor 742, the home sensor 743, and the second limit sensor 744 are sensors that detect the position of the slider 720 that moves on the rail of the linear guide 740. Signals detected by the sensors are input to the pump control unit 710.

The home sensor 743 is a sensor used for determining an initial position (hereinafter also referred to as home position) of the slider 720 on the linear guide 740. The home position is a position where the slider 720 is held when work such as attachment and replacement of the fluid container 760 is performed.

The residual amount sensor 742 is a sensor for detecting the position of the slider 720 (hereinafter also referred to as residual amount position) where the residual amount of the fluid in the fluid container 760 is equal to or smaller than a predetermined value when the slider 720 moves in the push-in direction of the plunger 762 from the home position. When the slider 720 moves to the residual amount position where the residual amount sensor 742 is provided, predetermined an alarm is output to the operator (the surgeon or an assistant). The operator determines to perform work for replacing the fluid container 760 currently in use with a new fluid container 760 at appropriate timing. Alternatively, when the auxiliary second pump 700b having the same configuration as the pump 700 (the first pump 700a) is prepared, switching work is performed to supply the fluid to the pulsation generator 100 from the auxiliary second pump 700b.

The first limit sensor 741 indicates a limit position (hereinafter also referred to as first limit position) in a movable range of the slider 720 moving in the push-in direction of the plunger 762 from the home position. When the slider 720 moves to the first limit position where the first limit sensor 741 is provided, the residual amount of the fluid in the fluid container 760 is smaller than the residual amount at the time when the slider 720 is in the residual amount position. A predetermined alarm is output to the operator. In this case as well, the work for replacing the fluid container 760 currently in use with the new fluid container 760 or the switching work to the auxiliary second pump 700b is performed.

On the other hand, the second limit sensor 744 indicates a limit position (hereinafter also referred to as second limit position) of the movable range of the slider 720 moving in the opposite direction of the push-in direction of the plunger 762 from the home position. The predetermined alarm is also output when the slider 720 moves to the second limit position where the second limit sensor 744 is provided.

A touch sensor 723 and a pressure sensor (a pressure detecting unit) 722 are attached to the slider 720.

The touch sensor 723 is a sensor for detecting whether the slider 720 is in contact with the plunger 762 of the fluid container 760.

The pressure sensor 722 is a sensor that detects the pressure of the fluid in the fluid storing unit 765 formed by the inner wall of the syringe 761 and the gasket 763, that is, the pressure of the slider 720 in pressing the fluid storing unit 765 and outputs a signal (a detection signal) of a level (e.g., a voltage, an electric current, or a frequency) corresponding to the pressure.

When the slider 720 is moved in the push-in direction in a state in which the pinch valve 750 is closed, after the slider 720 comes into contact with the plunger 762, the pressure of the fluid in the fluid storing unit 765 rises as a push-in amount of the slider 720 is increased.

On the other hand, when the slider 720 is moved in the push-in direction in a state in which the pinch valve 750 is opened, even after the slider 720 comes into contact with the plunger 762, the fluid in the fluid storing unit 765 flows out from the nozzle 211 of the pulsation generator 100 through the connection tube 25. Therefore, the pressure of the fluid in the fluid storing unit 765 rises to a certain degree but does not rise even if the slider 720 is further moved in the push-in direction.

Note that signals from the touch sensor 723 and the pressure sensor 722 are input to the pump control unit 710.

In the following explanation, the slider 720, the motor 730, and the linear guide 740 are sometimes referred to as fluid pressing unit 731. The fluid pressing unit 731 presses the fluid storing unit 765 and causes the fluid to flow out from the opening section (fluid outlet) 764 of the fluid container 760.

A preparation operation for attaching the fluid container 760, in which the fluid is filled, to the fluid-container attaching unit 770 anew, supplying the fluid in the fluid container 760 to the pulsation generator 100, and enabling the fluid to be ejected from the pulsation generator 100 in a pulse-like manner is explained.

First, the operator operates the slider release switch 780 to input an ON signal of the slider release switch 780 to the pump control unit 710. Then, the pump control unit 710 moves the slider 720 to the home position.

The operator attaches the fluid container 760, which is connected to the connection tube 25 beforehand, to the fluid-container attaching unit 770. Note that the fluid is already filled in the syringe 761 of the fluid container 760.

After setting the connection tube 25 in the pinch valve 750, when the operator operates the pinch valve switch 785 to input an ON signal of the pinch valve switch 785 to the pump control unit 710, the pump control unit 710 closes the pinch valve 750.

Subsequently, the operator operates the slider set switch 781 to input an ON signal of the slider set switch 781 to the pump control unit 710. Then, the pump control unit 710 moves the slider 720 in the push-in direction and starts control to set the pressure of the fluid stored in the fluid storing unit 765 in the fluid container 760 to a predetermined target pressure value determined according to ejecting strength set by the ejecting-strength changeover switch 627.

Thereafter, when the fluid-feed ready switch 782 is pressed by the operator, an ON signal of the fluid-feed ready switch 782 is input to the pump control unit 710. When the pressure of the fluid in the fluid storing unit 765 is within a specified range (hereinafter also referred to as rough window) with respect to the target pressure value, the pump control unit 710 changes to a fluid feedable state in which feeding of the fluid from the pump 700 to the pulsation generator 100 is permitted.

In the fluid feedable state of the pump control unit 710, when an ON signal of the priming switch 783 is input to the pump control unit 710 by the operation by the operator, the pump control unit 710 starts priming processing. The priming processing is processing for filling a channel of the fluid from the fluid container 760 to the connection tube 25 and a fluid-ejecting opening section 212 of the pulsation generator 100 with the fluid.

When the priming processing is started, the pump control unit 710 opens the pinch valve 750 and starts movement in the push-in direction of the slider 720 at timing simultaneous or substantially simultaneous with the opening of the pinch valve 750 (e.g., with a time difference of about several milliseconds to several tens milliseconds). The movement of the slider 720 is performed at predetermined speed at which a delivery amount per unit time of the fluid from the fluid container 760 is fixed. The priming processing is performed until a predetermined time required for the priming processing elapses (or the slider 720 moves a predetermined distance) or until the operator operates the priming switch 783 to input an OFF signal.

Consequently, a predetermined amount of the fluid in the fluid storing unit 765 is delivered from the pump 700 at predetermined flow velocity (an ejection amount of the fluid per unit time) and fills the inside of the connection tube 25 from the pinch valve 750 to the pulsation generator 100 and also fills the fluid chamber 501 of the pulsation generator 100, the fluid ejecting pipe 200, and the like. Note that the air present in the connection tube 25 and the pulsation generator 100 before the start of the priming processing is emitted to the atmosphere from the nozzle 211 of the pulsation generator 100 as the fluid flows into the connection tube 25 and the pulsation generator 100.

Note that the predetermined speed, the predetermined distance, or the predetermined time for moving the slider 720 in the priming processing is stored in the pump control unit 710 beforehand.

In this way, the priming processing is completed.

Subsequently, when an ON signal of the flushing switch 628 is input to the driving control unit 600 by the operation by the operator, the driving control unit 600 and the pump control unit 710 start degassing processing.

The degassing processing is processing for discharging air bubbles remaining in the connection tube 25 and the pulsation generator 100 from the nozzle 211 of the pulsation generator 100.

In the degassing processing, in a state in which the pinch valve 750 is opened, the pump control unit 710 moves the slider 720 in the push-in direction at predetermined speed for fixing a delivery amount per unit time of the fluid from the fluid container 760 and supplies the fluid to the pulsation generator 100. The driving control unit 600 drives the piezoelectric element 401 of the pulsation generator 100 in association with the ejection of the fluid by the pump 700 and ejects the fluid from the pulsation generator 100. Consequently, the air bubbles remaining in the connection tube 25 and the pulsation generator 100 are discharged from the nozzle 211 of the pulsation generator 100. The degassing processing is performed until a predetermined time elapses (or the slider 720 moves a predetermined distance) or until the operator operates the flushing switch 628 to input an OFF signal.

Note that the predetermined speed, the predetermined time, or the predetermined distance for moving the slider 720 in the degassing processing is stored in the driving control unit 600 and the pump control unit 710 beforehand.

When the degassing processing ends, the pump control unit 710 closes the pinch valve 750 and detects the pressure of the fluid stored in the fluid storing unit 765 of the fluid container 760. The pump control unit 710 performs control for adjusting the position of the slider 720 to set the pressure to the target pressure value determined according to the ejecting strength.

Thereafter, when the pressure of the fluid in the fluid storing unit 765 is within the specified range (the rough window) with respect to the target pressure value, the fluid can be ejected from the pulsation generator 100 in a pulse-like manner.

In this state, when the pulsation-generating-unit start switch 625 is operated by the foot of the surgeon and an ON signal of the pulsation-generating-unit start switch 625 is input to the driving control unit 600, according to a signal transmitted from the driving control unit 600, the pump control unit 710 opens the pinch valve 750, moves the slider 720 in the push-in direction at predetermined speed at timing simultaneous or substantially simultaneous with the opening of the pinch valve 750 (e.g., with a time difference of several milliseconds to several tens milliseconds), and starts the supply of the fluid to the pulsation generator 100. On the other hand, the driving control unit 600 starts the driving of the piezoelectric element 401 and changes the volume of the fluid chamber 501 to generate a pulsed flow. In this way, the fluid is ejected from the nozzle 211 at the distal end of the pulsation generator 100 in a pulse-like manner at high speed.

Thereafter, when the surgeon operates the pulsation-generating-unit start switch 625 by foot and an OFF signal of the pulsation-generating-unit start switch 625 is input to the driving control unit 600, the driving control unit 600 stops the driving of the piezoelectric element 401. According to a signal transmitted from the driving control unit 600, the pump control unit 710 stops the movement of the slider 720 and closes the pinch valve 750. In this way, the ejecting of the fluid from the pulsation generator 100 stops.

Note that, the pump 700 according to this embodiment has the configuration in which the slider 720 presses the fluid container 760 configured as the injection cylinder including the syringe 761 and the plunger 762. However, the pump 700 may have a configuration shown in FIG. 4.

Figure 4:
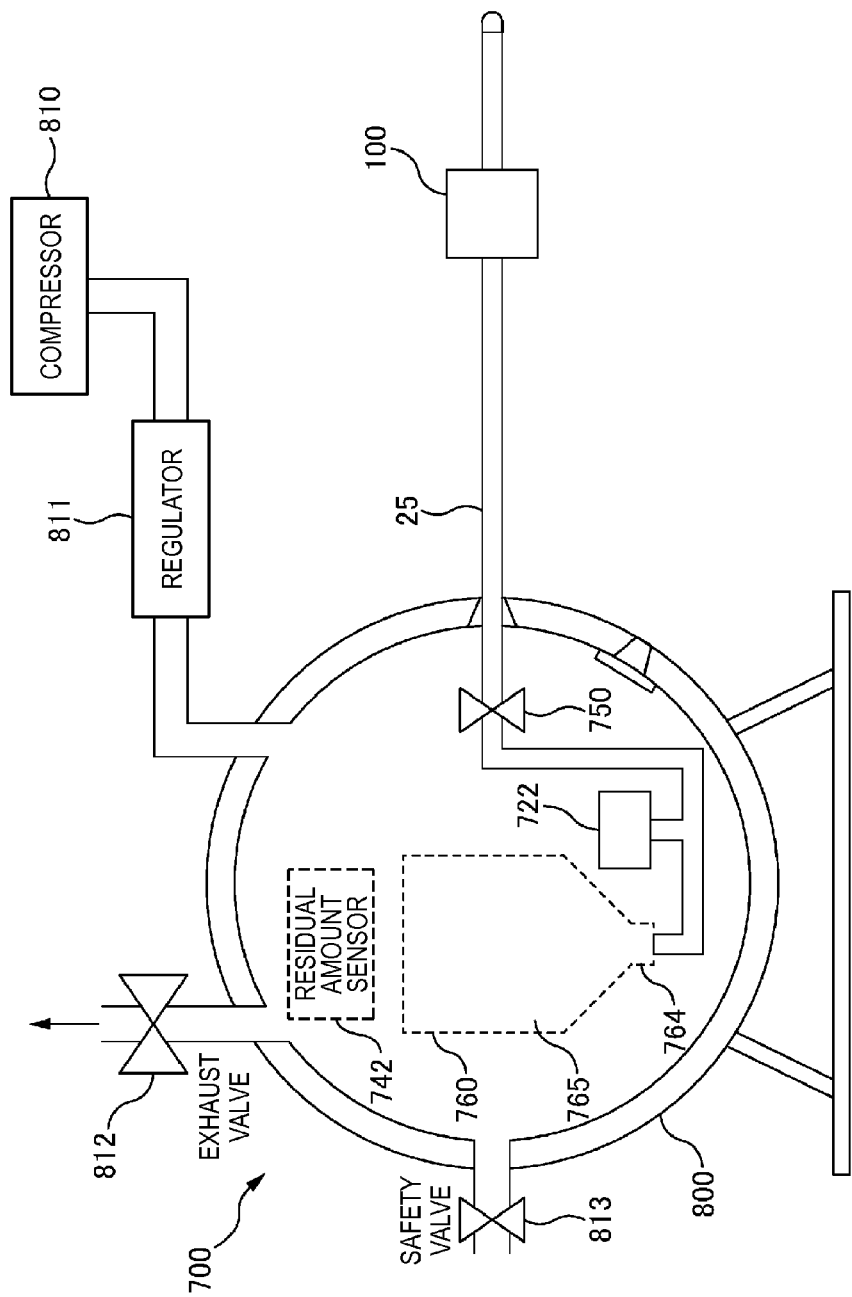
FIG. 4 is a block diagram showing the configuration of the pump according to the embodiment of the invention.

The pump 700 shown in FIG. 4 has a configuration in which the fluid container 760 configured as an infusion fluid bag, which stores the fluid, is attached in a pressurization chamber 800 and, after the air supplied from a compressor 810 is smoothed by a regulator 811, the air is pressure-fed into the pressurization chamber 800 to press the fluid container 760.

In a state in which the air in the pressurization chamber 800 is pressurized to press the fluid container 760, when the pinch valve 750 is opened, the fluid stored in the fluid storing unit 765 of the fluid container 760 flows out from the opening section 764 and is supplied to the pulsation generator 100 through the connection tube 25.

Note that the air in the pressurization chamber 800 is emitted to the atmosphere by opening an exhaust valve 812. When the pressure of the air in the pressurization chamber 800 exceeds predetermined pressure, even if the exhaust valve 812 is not opened, the air in the pressurization chamber 800 is emitted to the atmosphere when a safety valve 813 opens.

Note that, although not shown in FIG. 4, the compressor 810, the regulator 811, the exhaust valve 812, and the pinch valve 750 are controlled by the pump control unit 710.

Detection signals output from the pressure sensor 722 that detects the pressure of the fluid in the fluid container 760 and the residual amount sensor 742 that detects the residual amount of the fluid in the fluid container 760 are also input to the pump control unit 710.

In the case of the pump 700 shown in FIG. 4, the compressor 810, the regulator 811, and the pressurization chamber 800 configure the fluid pressing unit 731.

By adopting the pump 700 having such a form, it is possible to increase an amount of the fluid that can be supplied to the pulsation generator 100 per unit time. It is also possible to supply the fluid at high pressure with the pulsation generator 100. Further, since the infusion fluid bag, which stores the fluid, is directly used as the fluid container 760, it is possible to prevent contamination of the fluid. It is also possible to continuously feed the fluid to the pulsation generator 100 without causing pulsation.

Besides, in this embodiment, the driving control unit 600 is disposed in a position separated from the pump 700 and the pulsation generator 100. However, the driving control unit 600 may be configured integrally with the pump 700.

When a surgical operation is performed using the fluid ejection device 1, a part griped by the surgeon is the pulsation generator 100. Therefore, the connection tube 25 to the pulsation generator 100 is desirably as flexible as possible. It is desirable that the connection tube 25 is a flexible and thin tube and the ejection pressure of the fluid from the pump 700 is set to low pressure in a range in which the fluid can be fed to the pulsation generator 100. Therefore, the ejection pressure of the pump 700 is set to approximately 0.3 atm (0.03 MPa) or less.

In particular, when there is a risk that a failure of an apparatus causes a serious accident as in brain surgery, spouting of high-pressure fluid in cutting or the like of the connection tube 25 has to be avoided. Therefore, it is also requested to keep the ejection pressure from the pump 700 at low pressure.

Pulsation generator

The structure of the pulsation generator 100 according to this embodiment is explained.

Figure 5:
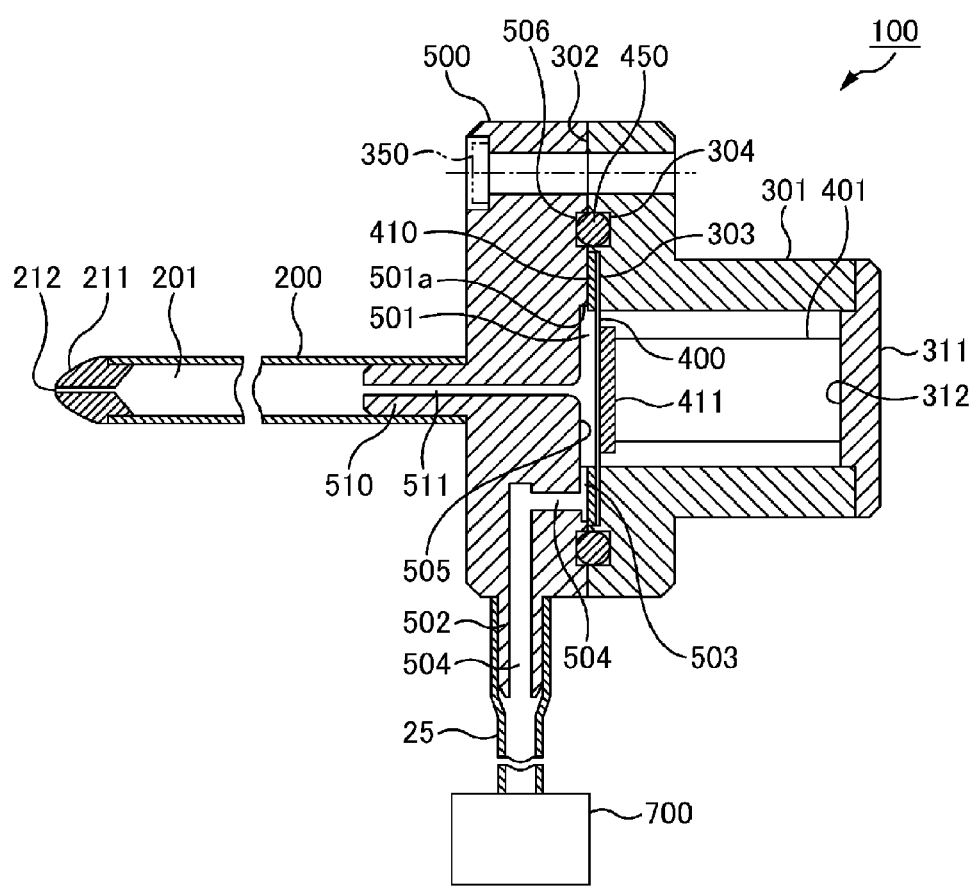
FIG. 5 is a sectional view showing the structure of a pulsation generator according to the embodiment of the invention.

FIG. 5 is a sectional view showing the structure of the pulsation generator 100 according to this embodiment. In FIG. 5, the fluid ejecting pipe 200 including a pulsation generating unit configured to generate pulsation of the fluid and including a connection channel 201 functioning as a channel for ejecting the fluid is connected to the pulsation generator 100.

In the pulsation generator 100, an upper case 500 and a lower case 301 are respectively joined on surfaces opposed to each other. The upper case 500 and the lower case 301 are screwed by four fixing screws 350 (not shown in the figure). The lower case 301 is a cylindrical member having a brim section. One end portion of the lower case 301 is closed by a bottom plate 311. The piezoelectric element 401 is disposed in the inner space of the lower case 301.

The piezoelectric element 401 is a stacked piezoelectric element and configures an actuator. One end portion of the piezoelectric element 401 is fixedly attached to the diaphragm 400 via a top plate 411. The other end portion of the piezoelectric element 401 is fixedly attached to an upper surface 312 of the bottom plate 311.

The diaphragm 400 is made of a disk-like metal thin plate. In a recessed section 303 of the lower case 301, a circumferential edge portion of the diaphragm 400 is closely attached and fixedly attached to the bottom surface of a recessed section 303. By inputting a drive signal to the piezoelectric element 401 functioning as a volume varying unit, the volume of the fluid chamber 501 is changed via the diaphragm 400 according to expansion and contraction of the piezoelectric element 401.

On the upper surface of the diaphragm 400, a reinforcing plate 410 made of a disk-like metal thin plate having an opening section in the center is stacked and disposed.

In the upper case 500, a recessed section is formed in the center of the surface opposed to the lower case 301. A rotating body shape configured from the recessed section and the diaphragm 400 and filled with the fluid is the fluid chamber 501. That is, the fluid chamber 501 is a space surrounded by a sealing surface 505 and an inner circumferential sidewall 501a of the recessed section of the upper case 500 and the diaphragm 400. An outlet channel 511 is drilled in substantially the center of the fluid chamber 501.

The outlet channel 511 is pierced from the fluid chamber 501 to an end portion of an outlet cannel pipe 510 projected from one end face of the upper case 500. A connecting section of the outlet channel 511 to the sealing surface 505 of the fluid chamber 501 is smoothly rounded in order to reduce fluid resistance.

Note that, in this embodiment (see FIG. 5), the shape of the fluid chamber 501 explained above is a substantially cylindrical shape sealed at both ends. However, the shape may be a conical shape or a trapezoidal shape or may be a semispherical shape or the like in side view and is not limited to the cylindrical shape. For example, if the connecting section of the outlet channel 511 and the sealing surface 505 is formed in a shape like a funnel, it is easy to discharge air bubbles in the fluid chamber 501 explained below.

The fluid ejecting pipe 200 is connected to the outlet channel pipe 510. The connection channel 201 is drilled in the fluid ejecting pipe 200. The diameter of the connection channel 201 is larger than the diameter of the outlet channel 511. The thickness of a pipe section of the fluid ejecting pipe 200 is set in a range in which the pipe section has rigidity for not absorbing pressure pulsation of the fluid.

The nozzle 211 is inserted into the distal end portion of the fluid ejecting pipe 200. The fluid-ejecting opening section 212 is drilled in the nozzle 211. The diameter of the fluid-ejecting opening section 212 is smaller than the diameter of the connection channel 201.

On the side surface of the upper case 500, an inlet channel pipe (a fluid intake port) 502, into which the connection tube 25 for supplying the fluid from the pump 700 is inserted, is projected. A connection channel 504 on an inlet channel side is drilled in the inlet channel pipe 502. The connection channel 504 communicates with an inlet channel 503. The inlet channel 503 is formed in a groove shape in the circumferential edge portion of the sealing surface 505 of the fluid chamber 501 and communicates with the fluid chamber 501.

On the joining surface of the upper case 500 and the lower case 301, in a separated position in the outer circumferential direction of the diaphragm 400, a packing box 304 is formed on the lower case 301 side and a packing box 506 is formed on the upper case 500 side. A ring-like packing 450 is attached in a space formed by the packing boxes 304 and 506.

When the upper case 500 and the lower case 301 are assembled, the circumferential edge portion of the diaphragm 400 and the circumferential edge portion of the reinforcing plate 410 are closely set in contact with the circumferential edge portion of the sealing surface 505 of the upper case 500 by the bottom surface of the recessed section 303 of the lower case 301. In this case, the packing 450 is pressed by the upper case 500 and the lower case 301 to prevent a fluid leak from the fluid chamber 501.

When the fluid is ejected, the inside of the fluid chamber 501 is in a high pressure state of 30 atm (3 MPa) or higher. It is likely that the fluid slightly leaks in joining sections of the diaphragm 400, the reinforcing plate 410, the upper case 500, and the lower case 301. However, the leak is prevented by the packing 450.

When the packing 450 is disposed as shown in FIG. 5, the packing 450 is compressed by the pressure of the fluid leaking from the fluid chamber 501 at high pressure. The packing 450 is more strongly pressed against the walls in the packing boxes 304 and 506. Therefore, it is possible to more surely prevent the leak of the fluid. Consequently, it is possible to maintain a high pressure rise in the fluid chamber 501 during driving.

Figure 6:
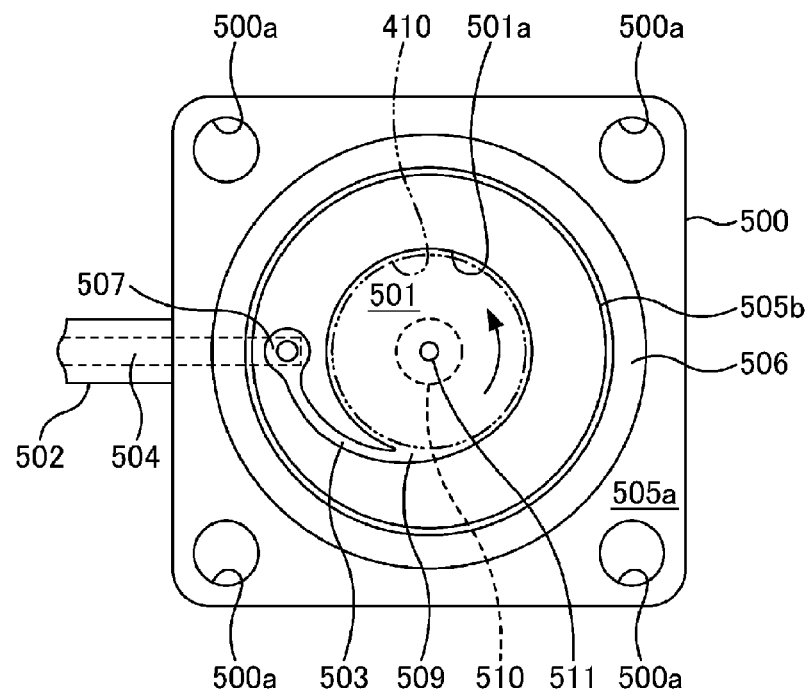
FIG. 6 is a plan view showing a form of an inlet channel according to the embodiment of the invention.

The inlet channel 503 formed in the upper case 500 is explained more in detail with reference to FIG. 6.

FIG. 6 is a plan view showing a form of the inlet channel 503. A state in which the upper case 500 is viewed from the joining surface side with the lower case 301 is shown.

In FIG. 6, the inlet channel 503 is formed in a circumferential edge groove shape of the sealing surface 505 of the upper case 500.

One end portion of the inlet channel 503 communicates with the fluid chamber 501. The other end portion of the inlet channel 503 communicates with the connection channel 504. A fluid reservoir 507 is formed in a connecting section of the inlet channel 503 and the connection channel 504. A connecting section of the fluid reservoir 507 and the inlet channel 503 is smoothly rounded to reduce fluid resistance.

The inlet channel 503 communicates with the inner circumferential sidewall 501a of the fluid chamber 501 toward a substantially tangential direction. The fluid supplied from the pump 700 (see FIG. 1) at predetermined pressure flows along the inner circumferential sidewall 501a (in a direction indicated by an arrow in FIG. 6) to generate a swirl flow in the fluid chamber 501. The swirl flow is pressed to the inner circumferential sidewall 501a side with a centrifugal force by swirling. The air bubbles included in the fluid chamber 501 concentrate on the center of the swirl flow.

The air bubbles collected in the center are removed from the outlet channel 511. Therefore, it is more desirable to provide the outlet channel 511 in the vicinity of the center of the swirl flow, that is, in the axial center of a rotating body shape.

As shown in FIG. 6, the inlet channel 503 is curved. The inlet channel 503 may communicate with the fluid chamber 501 along a straight line without being curved. However, the inlet channel 503 is curved to increase channel length and obtain desired inertance (explained below) in a narrow space.

Note that, as shown in FIG. 6, the reinforcing plate 410 is disposed between the diaphragm 400 and the circumferential edge portion of the sealing surface 505 in which the inlet channel 503 is formed. The reinforcing plate 410 is provided to improve durability of the diaphragm 400. A cutout-like connection opening section 509 is formed in a connecting section of the inlet channel 503 to the fluid chamber 501. Therefore, when the diaphragm 400 is driven at a high frequency, it is likely that stress concentration occurs in the vicinity of the connection opening section 509 to cause fatigue fracture. Therefore, the reinforcing plate 410 having a continuous opening section without a cutout section is disposed to prevent stress concentration from occurring in the diaphragm 400.

In the outer circumferential corner portions of the upper case 500, screw holes 500a are opened in four places. The upper case 500 and the lower case 301 are screwed and joined in the positions of the screw holes.

Note that, although not shown in the figure, the reinforcing plate 410 and the diaphragm 400 can be joined and integrally stacked and fixedly attached. A method of fixedly attaching the reinforcing plate 410 and the diaphragm 400 may be a method of sticking the reinforcing plate 410 and the diaphragm 400 using an adhesive or may be a method such as solid phase diffusion joining or welding. However, the reinforcing plate 410 and the diaphragm 400 are more desirably closely attached on a joining surface.

Operation of the Pulsation Generator

The operation of the pulsation generator 100 in this embodiment is explained with reference to FIGS. 1 to 6. Fluid ejection by the pulsation generator 100 in this embodiment is performed by a difference between inertance L1 (sometimes referred to as combined inertance L1) on the inlet channel 503 side and inertance L2 (sometimes referred to as combined inertance L2) on the outlet channel 511 side.

Inertance

First, the inertance is explained.

When the density of the fluid is represented as p, the sectional area of a channel is represented as S, and the length of the channel is represented as h, inertance L is represented by $L = \rho \times h / S$. When a pressure difference of the channel is represented as $\Delta P$ and a flow rate of the fluid flowing through the channel is represented as Q, by transforming an equation of motion in the channel using the inertance L, a relation of $\Delta P = L \times dQ/dt$ is derived.

That is, the inertance L indicates a degree of influence on a temporal change of the flow rate. The temporal change of the flow rate is smaller as the inertance is larger. The temporal change of the flow rate is larger as the inertance L is smaller.

Combined inertance concerning parallel connection of a plurality of channels and series connection of a plurality of channels having different shapes can be calculated by combining inertances of respective channels in the same manner as parallel connection or series connection of inductances in an electric circuit.

Note that, since the diameter of the connection channel 504 is set sufficiently large with respect to the diameter of the inlet channel 503, the inertance L1 on the inlet channel 503 side is calculated in a range of the inlet channel 503. In this case, since the connection tube 25 that connects the pump 700 and the inlet channel 503 has flexibility, the connection tube 25 maybe excluded from the calculation of the inertance L1.

Since the diameter of the connection channel 201 is far larger than the diameter of the outlet channel 511 and the thickness of the pipe section (the pipe wall) of the fluid ejecting pipe 200 is small, the influence of the diameter of the connection channel 201 and the thickness of the pipe section of the fluid ejecting pipe 200 on the inertance L2 is very small. Therefore, the inertance L2 on the outlet channel 511 side may be replaced with the inertance of the outlet channel 511.

Note that the pipe wall of the fluid ejecting pipe 200 has sufficient rigidity for pressure propagation of the fluid.

In this embodiment, the channel length and the sectional area of the inlet channel 503 and the channel length and the sectional area of the outlet channel 511 are set such that the inertance L1 on the inlet channel 503 side is larger than the inertance L2 on the outlet channel 511 side.

Ejecting of the Fluid

The operation of the pulsation generator 100 is explained below.

The fluid is supplied to the inlet channel 503 by the pump 700 at given pressure. As a result, when the piezoelectric element 401 does not perform an operation, the fluid flows in the fluid channel 501 with a difference between an ejection force of the pump 700 and a fluid resistance value of the entire inlet channel 503 side.

When a drive signal is input to the piezoelectric element 401 and the piezoelectric element 401 suddenly expands, the pressure in the fluid chamber 501 quickly rises and reaches several tens atm if the inertances L1 and L2 on the inlet channel 503 side and the outlet channel 511 side have sufficient magnitude.

The pressure in the fluid chamber 501 is far larger than the pressure by the pump 700 applied to the inlet channel 503. Therefore, inflow of the fluid into the fluid chamber 501 from the inlet channel 503 side decreases and outflow from the outlet channel 511 increases because of the pressure.

Since the inertance L1 of the inlet channel 503 is larger than the inertance L2 of the outlet channel 511, an increase in amount of the fluid ejected from the outlet channel 511 is larger than a decrease amount of the flow rate of the fluid flowing into the fluid chamber 501 from the inlet channel 503. Therefore, pulse-like fluid ejection, that is, a pulsed flow occurs in the connection channel 201. Pressure fluctuation in the ejection propagates through the fluid ejecting pipe 200. The fluid is ejected from the fluid-ejecting opening section 212 of the nozzle 211 at the distal end.

Since the diameter of the fluid-ejecting opening section 212 of the nozzle 211 is smaller than the diameter of the outlet channel 511, the fluid is ejected as pulse-like droplets at higher pressure and higher speed.

On the other hand, the inside of the fluid chamber 501 changes to a decompressed state immediately after a pressure rise because of interaction of a decrease in a fluid inflow amount from the inlet channel 503 and an increase in a fluid outflow from the outlet channel 511. As a result, a flow of the fluid in the inlet channel 503 flowing to the fluid chamber 501 at speed same as the speed before the operation of the piezoelectric element 401 is restored after the elapse of a predetermined time by both of the pressure of the pump 700 and the decompressed state in the fluid chamber 501.

After the flow of the fluid in the inlet channel 503 is restored, if the piezoelectric element 401 expands, it is possible to continuously eject the pulsed flow from the nozzle 211.

Removal of the Air Bubbles

A removing operation for the air bubbles in the fluid chamber 501 is explained.

As explained above, the inlet channel 503 communicates with the fluid chamber 501 through the route approaching the fluid chamber 501 while turning around the fluid chamber 501. The outlet channel 511 is opened in the vicinity of the rotation axis of the substantial rotating body shape of the fluid chamber 501.

Therefore, the fluid flowing into the fluid chamber 501 from the inlet channel 503 swirls along the inner circumferential sidewall 501a in the fluid chamber 501. The fluid is pressed to the inner circumferential sidewall 501a side of the fluid chamber 501 by a centrifugal force. Air bubbles included in the fluid concentrate on the center of the fluid chamber 501. As a result, the air bubbles are discharged from the outlet channel 511.

Therefore, even in a very small volume change of the fluid chamber 501 due to the piezoelectric element 401, the pressure fluctuation is not hindered by the air bubbles and a sufficient pressure rise is obtained.

According to this embodiment, since the fluid is supplied to the inlet channel 503 by the pump 700 at predetermined pressure, the fluid is supplied to the inlet channel 503 and the fluid chamber 501 even in a state in which the driving of the pulsation generator 100 is stopped. Therefore, it is possible to start an initial operation even if a priming water operation is not performed.

Since the fluid is ejected from the fluid-ejecting opening section 212 further reduced than the diameter of the outlet channel 511, fluid pressure is higher than the fluid pressure in the outlet channel 511. Therefore, it is possible eject the fluid at high speed.

Further, the fluid ejecting pipe 200 has rigidity enough for transmitting the pulsation of the fluid fed from the fluid chamber 501 to the fluid-ejecting opening section 212. Therefore, there is an effect that it is possible to eject a desired pulsed flow without hindering pressure propagation of the fluid from the pulsation generator 100.

Since the inertance of the inlet channel 503 is set larger than the inertance of the outlet channel 511, an increase in an outflow amount larger than a decrease in an inflow amount of the fluid to the fluid chamber 501 from the inlet channel 503 occurs in the outlet channel 511. Pulse-like fluid ejection into the fluid ejecting pipe 200 can be performed. Therefore, there is an effect that a check valve does not have to be provided on the inlet channel 503 side, the structure of the pulsation generator 100 can be simplified, cleaning of the inside is easy, and a concern about durability due to the use of the check valve can be eliminated.

Note that, if the volume of the fluid chamber 501 is suddenly reduced by setting the inertances of both of the inlet channel 503 and the outlet channel 511 sufficiently large, it is possible to suddenly increase the pressure in the fluid chamber 501.

By generating pulsation using the piezoelectric element 401 functioning as the volume varying unit and the diaphragm 400, it is possible to realize simplification of the structure of the pulsation generator 100 and a reduction in size involved in the simplification. A maximum frequency of a volume change of the fluid chamber 501 can be set to a high frequency equal to or higher than 1 KHz. This is optimum for ejecting of a high-speed pulsed flow.

The pulsation generator 100 generates a swirl flow in the fluid in the fluid chamber 501 with the inlet channel 503. Therefore, the pulsation generator 100 can push the fluid in the fluid chamber 501 in the outer circumferential direction of the fluid chamber 501 with a centrifugal force, concentrate the air bubbles included in the fluid on the center of the swirl flow, that is, in the vicinity of the axis of the substantial rotating body shape, and remove the air bubbles from the outlet channel 511 provided in the vicinity of the axis of the substantial rotating body shape. Consequently, it is possible to prevent a decrease in pressure amplitude due to the air bubbles held up in the fluid chamber 501 and continue stable driving of the pulsation generator 100.

Further, the inlet channel 503 is formed to communicate with the fluid chamber 501 through the route approaching the fluid chamber 501 while turning around the fluid chamber 501. Therefore, it is possible to generate the swirl flow without using a dedicated structure for swirling the fluid on the inside of the fluid chamber 501.

The groove-shaped inlet channel 503 is formed at the outer circumferential edge portion of the sealing surface 505 of the fluid chamber 501. Therefore, it is possible to form the inlet chamber 503 functioning as the swirl-flow generating unit without increasing the number of components.

Since the reinforcing plate 410 is provided on the upper surface of the diaphragm 400, the diaphragm 400 is driven with the opening section outer circumference of the reinforcing plate 410 as a fulcrum. Therefore, stress concentration less easily occurs. It is possible to improve the durability of the diaphragm 400.

Note that, if the corners of the joining surface of the reinforcing plate 410 to the diaphragm 400 are rounded, it is possible to further reduce the stress concentration of the diaphragm 400.

If the reinforcing plate 410 and the diaphragm 400 are stacked and integrally fixedly attached, it is possible to improve assemblability of the pulsation generator 100. Further, there is also a reinforcing effect of the outer circumferential edge portion of the diaphragm 400.

The fluid reservoir 507 for holding up the fluid is provided in the connecting section of the connection channel 504 and the inlet channel 503 on the inlet side to which the fluid is supplied from the pump 700. Therefore, it is possible to suppress the influence of the inertance of the connection channel 504 on the inlet channel 503.

Further, on the joining surface of the upper case 500 and the lower case 301, the ring-like packing 450 is provided in the position spaced apart in the outer circumferential direction of the diaphragm 400. Therefore, it is possible to prevent a leak of the fluid from the fluid chamber 501 and prevent a pressure drop in the fluid chamber 501.

Pressure Control in the Fluid Storing Unit

As explained above, in the fluid ejection device 1 according to this embodiment, when the ON signal of the pulsation-generating-unit start switch 625 is input to the driving control unit 600 by the surgeon, the pump 700 supplies of the fluid in the fluid storing unit 765 to the pulsation generator 100. The driving control unit 600 drives the piezoelectric element 401 to thereby eject the fluid from the pulsation generator 100 in a pulse-like manner.

It is important to perform the ejecting of the fluid from the pulsation generator 100 at appropriate strength intended by the surgeon. If the pressure of the fluid in the fluid storing unit 765 is too high, it is likely that ejecting strength of the fluid from the pulsation generator 100 increases and a target region is excessively cut.

Therefore, when the ON signal of the pulsation-generating-unit start switch 625 is input to the driving control unit 600, if the pressure of the fluid in the fluid storing unit 765 is lower than an upper limit value of the specified range (the rough window) determined with reference to the target pressure value determined according to the ejecting strength, the fluid ejection device 1 according to this embodiment ejects the fluid from the pulsation generator 100. However, if the pressure of the fluid in the fluid storing unit 765 is equal to or higher than the upper limit value, the fluid ejection device 1 does not eject the fluid from the pulsation generator 100.

Figure 7:
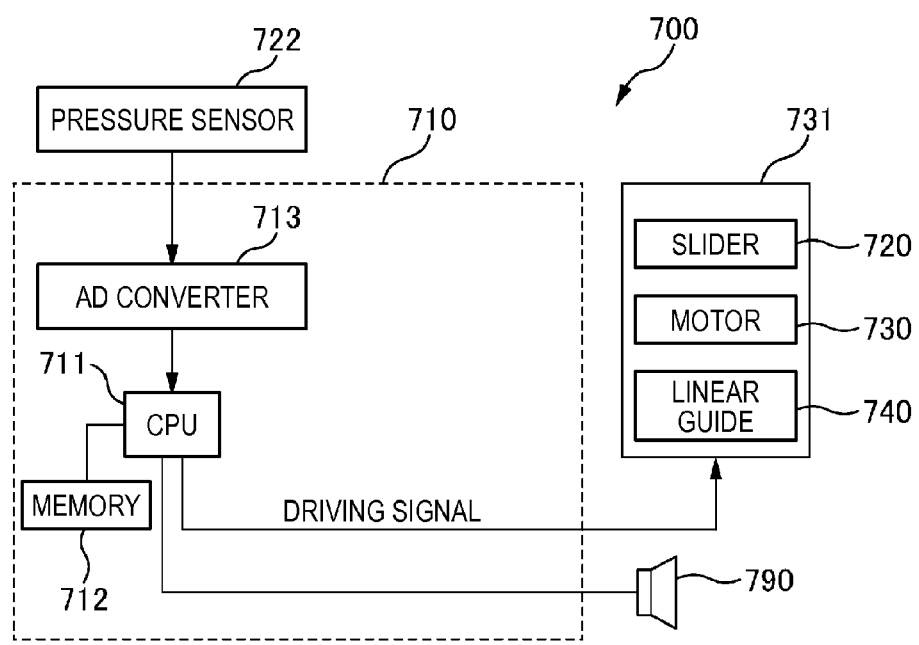
FIG. 7 is a block diagram showing the configuration of a pump control unit according to the embodiment of the invention.

The pressure control for the fluid storing unit 765 performed by the fluid ejection device 1 according to this embodiment is specifically explained with reference to FIGS. 7 to 9.

First, the configuration of the pump control unit (the pressing control unit) 710 is explained with reference to FIG. 7.

The pump control unit 710 includes a CPU (Central Processing Unit) 711, a memory 712, and an AD (Analog/Digital) converter 713.

The pump control unit 710 captures, from the pressure sensor 722, a detection signal of a level corresponding to pressure in the fluid storing unit 765 of the fluid container 760 and controls the fluid pressing section 731. For example, when the ON signal of the slider set switch 781 is input, the pump control unit 710 outputs a predetermined drive signal to the fluid pressing unit 731 to drive the motor 730 and controls the pressure to be the target pressure value. Note that the fluid pressing unit 731 includes a slider 720, a motor 730, and a linear guide 740.

The CPU 711 manages the control of the entire pump control unit 710. The CPU 711 executes a computer program configured from codes for performing various operations stored in the memory 712 to thereby realize the various functions according to this embodiment.

The memory 712 stores various data besides the computer program. For example, the memory 712 stores target pressure value level data indicating a level equivalent to the target pressure value, rough window upper limit value level data indicating a level equivalent to an upper limit value of the rough window (a first predetermined range), and rough window lower limit value level data indicating a level equivalent to a lower limit value of the rough window.

Further, the memory 712 stores fine window upper limit value level data indicating a level equivalent to an upper limit value of a fine window (a second predetermined range) explained below and fine window lower limit value level data indicating a level equivalent to a lower limit value of the fine window.

The AD converter 713 receives an input of a detection signal output from the pressure sensor 722 and outputs data indicating a level of the detection signal. Specifically, the pressure sensor 722 detects the pressure in the fluid storing unit 765 and outputs a detection signal of a level (e.g., a voltage) corresponding to the pressure. However, the AD converter 713 outputs detection level data (e.g., a voltage value) indicating the level of the detection signal output from the pressure sensor 722.

The CPU 711 captures the detection level data output from the AD converter 713 and compares the detection level data with various data stored in the memory 712.

For example, when the CPU 711 receives, from the driving control unit 600 via the communication cable 640, information to the effect that the ON signal of the pulsation-generating-unit start switch 625 is input to the driving control unit 600, if the detection level data output from the AD converter 713 is equal to or higher than the rough window upper limit value level data, the CPU 711 informs the driving control unit 600 to that effect via the communication cable 640. The driving control unit 600 does not output the drive signal to the pulsation generator 100.

In this way, if the pressure of the fluid in the fluid storing unit 765 is equal to or higher than the upper limit value of the specified range (the rough window) determined with reference to the target pressure value determined according to the ejecting strength, the fluid ejection device 1 according to this embodiment does not eject the fluid from the pulsation generator 100. Consequently, it is possible to improve the safety of the fluid ejection device 1.

Pressure control in the fluid storing unit 765 according to this embodiment is explained with reference to FIGS. 8 and 9.

Figure 8:
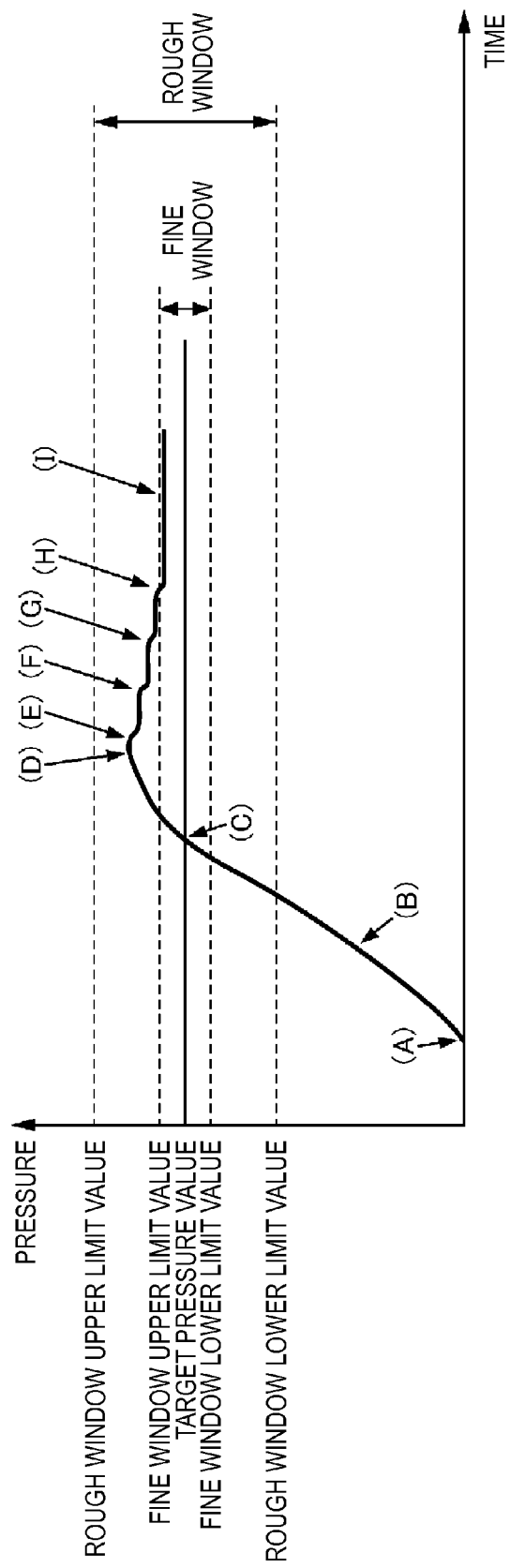
FIG. 8 is a diagram showing the transition of pressure according to the embodiment of the invention.

FIG. 8 is a diagram showing an example in which the pump control unit 710 performs control to bring the pressure in the fluid storing unit 765 close to the target pressure value determined according to the ejecting strength set by the ejecting strength changeover switch 627.

The pump control unit 710 stores, in the memory 712, for example, a table (not shown in the figure) in which ejecting strengths and target pressure values are associated. When receiving the ejecting strength set by the ejecting strength changeover switch 627 from the driving control unit 600 via the communication cable 640, the pump control unit 710 determines a target pressure value of the fluid storing unit 765 referring to the table.

For example, the pump control unit 710 determines, as a rough window upper limit value, a value obtained by adding a first predetermined value to the target pressure value and determines, as a rough window lower limit value, a value obtained by subtracting the first predetermined value from the target pressure value. Similarly, for example, the pump control unit 710 determines, as a fine window upper limit value, a value obtained by adding a second predetermined value smaller than the first predetermined value to the target pressure value and determines, as a fine window lower limit value, a value obtained by subtracting the second predetermined value from the target pressure value.

In this way, both of the fine window and the rough window are ranges of pressure determined with reference to the target pressure value. However, the range of the fine window is narrower than the range of the rough window.

The rough window is determined in, for example, a range of pressure in which ejecting strength can be varied in a range not causing a sense of discomfort with respect to ejecting strength designated by the surgeon.

Therefore, if the pressure in the fluid storing unit 765 is within the rough window (the first predetermined range), even if the pressure does not coincide with the target pressure value, the fluid ejection device 1 according to this embodiment performs the ejecting of the fluid from the pulsation generator 100 when the pulsation-generating-unit start switch 625 is operated. Consequently, for example, it is possible to start the ejecting without waiting for the end of the pressure adjustment in the fluid storing unit 765. It is possible to quickly and smoothly perform a surgical operation.

As explained above, if the pressure in the fluid storing unit 765 is equal to or higher than the upper limit value of the rough window, even if the pulsation-generating-unit start switch 625 is operated, the fluid ejection device 1 according to this embodiment does not perform the ejecting of the fluid from the pulsation generator 100. Consequently, it is possible to prevent strong ejecting not intended by the surgeon from being performed.

Similarly, if the pressure in the fluid storing unit 765 is equal to or lower than the lower limit value of the rough window, even if the pulsation-generating-unit start switch 625 is operated, the fluid ejection device 1 according to this embodiment does not perform the ejecting of the fluid from the pulsation generator 100. Consequently, it is possible to prevent useless ejecting that is too weak in ejecting strength to accurately perform incision, excision, and the like of a target region.

Note that, when the ejecting of the fluid is started in this way, as explained above, in order to start control to moves the slider 720 in the push-in direction at predetermined speed (speed at which a predetermined amount of the fluid flows out per unit time), the fluid ejection device 1 stops the control for bringing the pressure in the fluid storing unit 765 close to the target pressure value.

If the pressure in the fluid storing unit 765 is outside the rough window, even if the pulsation-generating-unit start switch 625 is operated, the fluid ejection device 1 does not perform the ejecting of the fluid from the pulsation generator 100. Consequently, it is possible to prevent the fluid from being ejected from the pulsation generator 100 at strength not intended by the surgeon. It is possible to improve the safety of the fluid ejection device 1.

When performing the control to bring the pressure in the fluid storing unit 765 close to the target pressure value, after the pressure in the fluid storing unit 765 once reaches the target pressure value, even if the pressure in the fluid storing unit 765 is different from the target pressure value, if the pressure is within the fine window (the second predetermined range), the fluid ejection device 1 does not perform the control for bringing the pressure close to the target pressure value. Consequently, it is possible to prevent the pump control unit 710 from continuously outputting the drive signal to the motor 730 to move the slider 720 irrespective of the fact that, for example, a difference between the pressure in the fluid storing unit 765 and the target pressure value is a very small difference that does not affect ejecting strength any more.

When performing the control to bring the pressure in the fluid storing unit 765 close to the target pressure value, after the pressure in the fluid storing unit 765 once reaches the target pressure value, if the pressure in the fluid storing unit 765 is within the rough window but is outside the fine window, the fluid ejection device 1 controls the fluid pressing unit 732 such that the pressure falls within the fine window.

Note that, in the following explanation, the control applied to the fluid pressing unit 732 by the pump control unit 710 if the pressure in the fluid storing unit 765 is within the rough window but is outside the fine window is also referred to fine adjustment.

When performing the fine adjustment, the pump control unit 710 outputs, to the fluid pressing unit 731, on a one-off basis, a drive signal for moving the slider 720 by a very small predetermined distance. After checking whether the pressure in the fluid storing unit 765 falls within the fine window, if the pressure in the fluid storing unit 765 is within the fine window, the pump control unit 710 ends the control. If the pressure in the fluid storing unit 765 is outside the fine window, the pump control unit 710 outputs again, on a one-off basis, the drive signal for moving the slider 720 by the very small predetermined distance.

(A) shown in FIG. 8 indicates a point in time when the slider 720 comes into contact with the plunger 762 and a rise of the pressure in the fluid storing unit 765 starts when the pump control unit 710 moves the slider 720 in the push-in direction.

At the point in time of (A) in FIG. 8, since the pressure in the fluid storing unit 765 is outside the range of the rough window, the pump control unit 710 controls the fluid pressing unit 731 such that the pressure in the fluid storing unit 765 coincides with the target pressure value.

In the following explanation, the control applied to the pump control unit 710 by the fluid pressing unit 732 such that the pressure coincides with the target pressure value if the pressure in the fluid storing unit 765 is outside the rough window is also referred to as rough adjustment.

When performing the rough adjustment, unlike the fine adjustment, the pump control unit 710 outputs the drive signal to continue the movement of the slider 720 until the pressure in the fluid storing unit 765 coincides with the target pressure value.

As shown indicated by (B) in FIG. 8, the pressure in the fluid storing unit 765 approaches the target pressure value according to the rough adjustment by the pump control unit 710.

When the pressure in the fluid storing unit 765 reaches the target pressure value ((C) in FIG. 8), the pump control unit 710 instructs the stop of the movement in the push-in direction of the slider 720. The slider 720 stops ((D) in FIG. 8).

Subsequently, the pump control unit 710 compares the pressure in the fluid storing unit 765 with the upper limit value and the lower limit value of the fine window and the upper limit value and the lower limit value of the rough window, respectively.

Specifically, the pump control unit 710 compares the detection level data output from the AD converter 713 with the rough window upper limit value level data, the rough window lower limit value level data, the fine window upper limit value level data, and the fine window lower limit value level data.

As shown in FIG. 8, if the pressure in the fluid storing unit 765 is equal to or higher than the upper limit value of the fine window but is lower than the upper limit value of the rough window, the pump control unit 710 starts the fine adjustment. In this case, the pump control unit 710 controls the fluid pressing unit 731 such that the pressure in the fluid storing unit 765 falls within the fine window.

When performing the fine adjustment, the pump control unit 710 repeatedly output, to the fluid pressing unit 731, a drive signal for moving the slider 720 by a very small predetermined distance. At timings of (E), (F), (G), and (H) in FIG. 8, the pump control unit 710 outputs the drive signal for performing the fine adjustment to the fluid pressing unit 731.

Thereafter, when the pressure in the fluid storing unit 765 falls within the fine window, the pump control unit 765 ends the fine adjustment ((I) in FIG. 8).

On the other hand, after the pressure in the fluid storing unit 765 reaches the target pressure value in (C) in FIG. 8, when the slider 720 stops, if the pressure in the fluid storing unit 765 is equal to or higher than the upper limit value of the rough window, the pump control unit 710 performs the rough adjustment again. In this case, the pump control unit 710 controls the fluid pressing unit 731 such that the pressure in the fluid storing unit 765 reaches the target pressure value.

Note that, since the gasket 763 attached to the distal end of the plunger 762 has elasticity, the pressure in the fluid storing unit 765 tends to continue to drop even after the stop of the slider 720 until the contraction of the gasket 763 stabilizes.

Therefore, after the pressure in the fluid storing unit 765 reaches the target pressure value in (C) in FIG. 8, when the slider 720 stops, even if the pressure in the fluid storing unit 765 is equal to or higher than the upper limit value of the rough window, thereafter, the pressure in the fluid storing unit 765 drops. Therefore, in some case, it is desirable to perform the fine adjustment rather than the rough adjustment. Consequently, it is possible to control the pressure in the fluid storing unit 765 to more accurately fall within the fine window.

For example, if the control for dropping the pressure in the fluid storing unit 765 is performed by the rough adjustment, even if the slider 720 is stopped when the pressure drops to the target pressure value, it is also likely that the overshoot occurs in which the pressure in the fluid storing unit 765 is far lower than the target pressure value. However, if the fine adjustment is performed, it is possible to prevent such a phenomenon.

Figure 9:
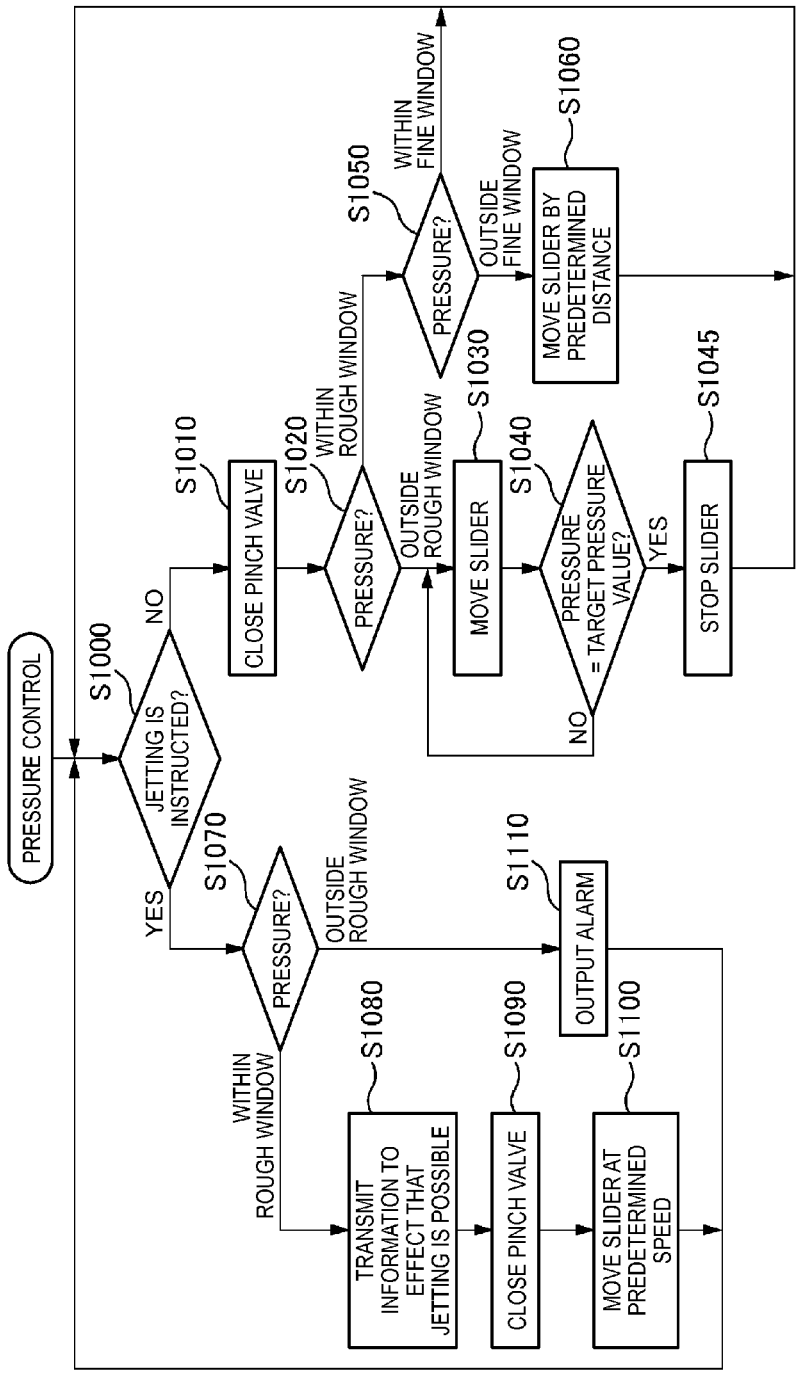
FIG. 9 is a flowchart for explaining a flow of processing of the fluid ejection device according to the embodiment of the invention.

FIG. 9 is a flowchart for explaining a flow of processing in which the CPU 711 performs control to bring the pressure in the fluid storing unit 765 close to the target voltage value determined according to the ejecting strength set by the ejecting-strength changeover switch 627.

First, the CPU 711 determines whether the ON signal of the pulsation-generating-unit start switch 625 is input to the driving control unit 600 (S1000).

If the ON signal of the pulsation-generating-unit start switch 625 is not input to the driving control unit 600, the CPU 711 closes the pinch valve 750 (S1010) and performs control to bring the pressure in the fluid storing unit 765 close to the target pressure value.

First, the CPU 711 determines whether the pressure in the fluid storing unit 765 is within the rough window (S1020).

If the pressure in the fluid storing unit 765 is equal to or higher than the upper limit value or equal to or lower than the lower limit value of the rough window, the CPU 710 determines that the pressure in the fluid storing unit 765 is outside the rough window.

If the pressure in the fluid storing unit 765 is outside the rough window, the CPU 711 performs the rough adjustment for moving the slider 720 such that the pressure in the fluid storing unit 765 coincides with the target pressure value (S1030 and S1040).

If the pressure in the fluid storing unit 765 coincides with the target pressure value, the CPU 711 stops the slider 720 (S1045).

Subsequently, if the pressure in the fluid storing unit 765 is within the rough window in 51020, the CPU 711 determines whether the pressure in the fluid storing unit 765 is within the fine window (S1050).

If the pressure in the fluid storing unit 765 is lower than the upper limit value or equal to or higher than the lower limit value of the fine window, the CPU 711 determines that the pressure in the fluid storing unit 765 is within the fine window. The CPU 711 does not perform the pressure control any more.

On the other hand, if the pressure in the fluid storing unit 765 is outside the fine window, the CPU 711 performs the fine adjustment such that the pressure in the fluid storing unit 765 falls within the fine window. Specifically, the CPU 711 outputs, to the fluid pressing unit 731, a drive signal for moving the slider 720 by a very small predetermined distance (S1060).

Consequently, the pressure in the fluid storing unit 765 is controlled to fall within the fine window.

On the other hand, if the ON signal of the pulsation-generating-unit start switch 625 is input to the driving control unit 600 in S1000, the CPU 711 determines whether the pressure in the fluid storing unit 765 is within the rough window (S1070).

If the pressure in the fluid storing unit 765 is within the rough window, the CPU 711 stops the pressure control (the rough adjustment and the fine adjustment) in the fluid storing unit 765 and transmits, to the driving control unit 600, information to the effect that the ejecting of the fluid from the pulsation generator 100 is possible (S1080). The driving control unit 600 outputs a drive signal to the piezoelectric element 401 and ejects the fluid from the pulsation generator 100 in a pulse-like manner.

The CPU 711 opens the pinch valve 750 (S1090) and starts control for moving the slider 720 in the push-in direction at predetermined speed (S1100).

On the other hand, if the pressure in the fluid storing unit 765 is outside the rough window in S1070, the CPU 711 outputs a predetermined alarm that indicates to that effect (S1110). For example, the CPU 711 emits predetermined alarm sound from the speaker 790. By outputting the predetermined alarm in this way, it is possible to inform the surgeon of a reason why the fluid is not ejected from the pulsation generator 100 irrespective of the face that the pulsation-generating-unit start switch 625 is operated.

In S1110, the CPU 711 transmits, to the driving control unit 600 via the communication cable 640, information to the effect that the pressure in the fluid storing unit 765 is outside the rough window and the ejecting is impossible. The driving control unit 600 does not output the drive signal to the piezoelectric element 401.

As explained above, in the fluid ejection device 1 according to this embodiment, if the pressure of the fluid in the fluid storing unit 765 is lower than the upper limit value of the specified range (the rough window) determined with reference to the target pressure value determined according to the ejecting strength, the driving control unit 600 outputs the drive signal to the pulsation generator 100. However, if the pressure of the fluid in the fluid storing unit 765 is equal to or higher than the upper limit value, the driving control unit 600 does not output the drive signal.

Consequently, if the pressure of the fluid in the fluid storing unit 765 is equal to or higher than the upper limit value of the rough window, it is possible to prevent the fluid from being ejected from the pulsation generator 100. It is possible to improve the safety of the fluid ejection device 1.

The embodiment is intended to facilitate understanding of the invention and not limitedly interpret the invention. The invention could be modified and improved without departing from the spirit of the invention. Equivalents of the invention are also included in the invention.

What is claimed is:

1. A fluid ejection device comprising:
    a fluid container including a fluid storing unit that stores fluid and a fluid outlet formed in the fluid storing unit;
    a fluid pressing unit configured to press the fluid storing unit and cause the fluid to flow out from the fluid outlet;
    a connection pipe, one end of which is connected to the fluid outlet;
    a fluid ejection unit including a fluid intake port, to which the other end of the connection pipe is connected, and configured to eject the fluid, which is taken in from the fluid intake port, in a pulse-like manner according to a drive signal;
    a pressure detecting unit configured to detect pressure in the fluid storing unit;
    an ejecting-strength input unit configured to receive an input for setting ejecting strength of the ejecting of the fluid by the fluid ejection unit;
    a pressing control unit configured to control the fluid pressing unit to bring the pressure in the fluid storing unit close to a target pressure value determined according to the ejecting strength;
    an ejecting-instruction input unit configured to receive an instruction input for ejecting the fluid from the fluid ejection unit; and
    a fluid-ejecting control unit configured to output the drive signal to the fluid ejection unit, wherein
    when the ejecting-instruction input unit receives the instruction input, if the pressure in the fluid storing unit is equal to or higher than an upper limit value in a first predetermined range determined with reference to the target pressure value, the fluid-ejecting control unit does not output the drive signal and, if the pressure in the fluid storing unit is lower than the upper limit value, the fluid-ejecting control unit outputs the drive signal.

2. The fluid ejection device according to claim 1, wherein, after the pressure in the fluid storing unit reaches the target pressure value, if the pressure is within a second predetermined range narrower than the first predetermined range determined with reference to the target pressure value, even if the pressure is different from the target pressure value, the pressing control unit does not perform the control for bringing the pressure close to the target pressure value.

3. The fluid ejection device according to claim 2, wherein, after the pressure in the fluid storing unit reaches the target pressure value, if the pressure is within the first predetermined range but is outside the second predetermined range, the pressing control unit controls the fluid pressing unit such that the pressure falls within the second predetermined range.

4. The fluid ejection device according to claim 1, wherein, while the fluid-ejecting control unit is outputting the drive signal, the pressing control unit controls the fluid pressing unit such that a predetermined amount of the fluid flows out per unit time from the fluid container.

5. The fluid ejection device according to claim 1, further comprising a channel opening and closing unit configured to open and close a channel of the fluid in the connection pipe, wherein
    the pressing control unit performs, by causing, in a state in which the channel is closed by the fluid opening and closing unit, the fluid pressing unit to press the fluid storing unit, the control for bringing the pressure in the fluid storing unit close to the target pressure value.

* * * * *